(12) United States Patent
Walter

(10) Patent No.: US 10,639,173 B2
(45) Date of Patent: May 5, 2020

(54) PERFORATED LINER

(71) Applicant: Uniprox GmbH & Co. KG, Zeulenroda-Triebes (DE)

(72) Inventor: Dennis Walter, Duderstadt (DE)

(73) Assignee: UNIPROX GMBH & CO. KG, Zeulenroda-Triebes (DE)

( * ) Notice: Subject to any disclaimer, the term of this patent is extended or adjusted under 35 U.S.C. 154(b) by 379 days.

(21) Appl. No.: 15/315,537

(22) PCT Filed: Jul. 21, 2015

(86) PCT No.: PCT/EP2015/066602
§ 371 (c)(1),
(2) Date: Dec. 1, 2016

(87) PCT Pub. No.: WO2016/012423
PCT Pub. Date: Jan. 28, 2016

(65) Prior Publication Data
US 2017/0239070 A1 Aug. 24, 2017

(30) Foreign Application Priority Data
Jul. 23, 2014 (DE) ................. 10 2014 011 034

(51) Int. Cl.
*A61F 2/78* (2006.01)
(52) U.S. Cl.
CPC .............. *A61F 2/7812* (2013.01); *A61F 2/78* (2013.01); *A61F 2002/785* (2013.01); *A61F 2002/7818* (2013.01)

(58) Field of Classification Search
CPC ........ A61F 2/5044; A61F 2/78; A61F 2/7812; A61F 2002/7818; A61F 2002/7837
See application file for complete search history.

(56) References Cited

U.S. PATENT DOCUMENTS

| | | | | |
|---|---|---|---|---|
| 4,832,010 A | * | 5/1989 | Lerman ................. | A61F 2/7812 602/63 |
| 5,888,231 A | * | 3/1999 | Sandvig ................ | A61F 2/7812 264/222 |
| 6,544,292 B1 | | 4/2003 | Laghi | |
| 2004/0260315 A1 | * | 12/2004 | Dell ...................... | A61F 2/0063 606/151 |
| 2007/0225824 A1 | | 9/2007 | Einarsson | |
| 2009/0036999 A1 | | 2/2009 | Egilsson et al. | |
| 2009/0082877 A1 | | 3/2009 | Einarsson | |

(Continued)

FOREIGN PATENT DOCUMENTS

| | | |
|---|---|---|
| DE | 38 20 098 A1 | 12/1989 |
| DE | 38 88 538 T2 | 10/1994 |

(Continued)

OTHER PUBLICATIONS

Carver, Adam. Development of a Prosthetic Liner with Air Channels: Honors Research Project. Apr. 22, 2011.*

(Continued)

*Primary Examiner* — Christie L Bahena
(74) *Attorney, Agent, or Firm* — Pearne & Gordon LLP

(57) ABSTRACT

The invention concerns a prosthesis liner for application to a limb stump, with an elastic liner layer (20) of elastomer, wherein the liner layer (20) has pores (26) in at least one distal portion (30) thereof.

9 Claims, 2 Drawing Sheets

(56) References Cited

U.S. PATENT DOCUMENTS

Figure 1:
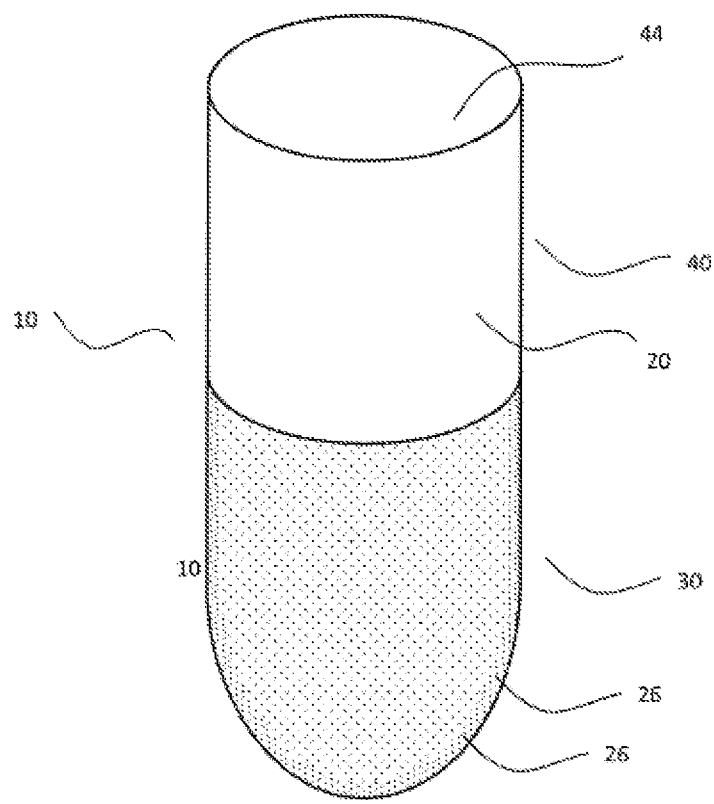

| | | | |
|---|---|---|---|
| 2011/0022171 A1* | 1/2011 | Richter | A61F 2/12 623/8 |
| 2012/0191218 A1 | 7/2012 | McCarthy | |
| 2013/0035770 A1 | 2/2013 | Egilsson et al. | |
| 2014/0379097 A1 | 12/2014 | Hurley et al. | |

FOREIGN PATENT DOCUMENTS

| | | |
|---|---|---|
| DE | 10 2007 035 409 A1 | 1/2009 |
| EP | 0 346 697 A2 | 12/1989 |
| EP | 1 263 356 B1 | 1/2010 |
| EP | 2 254 526 B1 | 9/2013 |
| WO | 2014/205403 A1 | 12/2014 |

OTHER PUBLICATIONS

Schulte, John. Prosthetic Socks. In Motion Magazine. vol. 11, Issue 2, pp. 29-31. Mar./Apr. 2001.*
International Search Report from Corresponding Application No. PCT/EP2015/066602; dated Sep. 15, 2015.
International Preliminary Report on Patentability from Corresponding Application No. PCT/EP2015/066602; dated Feb. 2, 2017.

* cited by examiner

PERFORATED LINER

FIELD OF THE INVENTION

The invention concerns an improved liner for prostheses for application to a limb stump. The invention constitutes an improvement in the wearing of the prosthesis.

BACKGROUND OF THE INVENTION

A missing limb of the body can be replaced by a prosthesis. The prosthesis mimics the function and/or the form of the missing limb. For the mechanical connection between prosthesis and stump of the limb, for example the shin stump or the thigh stump after amputation or exarticulation, the prosthesis comprises a so-called prosthesis shaft, which receives the limb stump and secures the prosthesis to the limb in a largely form-fitting and frictional-connecting way. Optionally, straps and similar means can also prevent the prosthesis shaft from slipping off of the limb stump.

For the fixation of the prosthesis shaft to the limb stump, a so-called liner is provided in particular, in the shape of a sock. As is known, this liner consists of an elastic material, silicone rubber or polyurethane or chloroprene-based polymer, especially RTV-silicone, a Shore A hardness of 20 to around 50. The prosthesis liner is pulled over the limb stump before putting on the prosthesis and forms a clinging, sealing and buffering intermediate layer between body and prosthesis shaft, which balances out the fitting inaccuracies which may occur in the course of the wearing and at the same time improves the wearing comfort.

In one embodiment of a prosthesis shaft, this is specifically adapted to the limb stump so that a fixation is facilitated. A frictional connection is accomplished by increasing the adhesive friction with adhesion promoting layers between the prosthesis shaft on the one hand and the skin surface of the limb stump on the other hand. One takes advantage of the fact that air is pressed out upon placing the prosthesis shaft on the limb stump, and the air can no longer flow back on account of the largely sealing action of the surfaces between limb stump and prosthesis shaft, so that an adhesion can be achieved.

An alternative but fundamentally related principle primarily takes advantage of the surface quality of the elastomer material of the liner, bringing about high friction on a skin surface of a limb, especially a hairless surface. As we know, certain elastomers such as silicone rubber or polyurethane or chloroprene-based polymers have an especially intimate adherence to the skin, especially when the elastomer is pressed against the skin surface, particularly on account of its inherent elasticity. A known prosthesis liner easily clings to the stump—with pretensioning by the naked limb stump—and it can absorb large shearing forces here. Thanks to additional means and measures, the adhering liner is mechanically connected to the rigid shaft of the prosthesis, for example by a distal metal base on the liner, which engages in a frictional-connecting and form-fitting manner with a corresponding structure on the prosthesis shaft. The prosthesis is thus held on firmly even without a vacuum forming primarily between stump and shaft.

In order to accomplish the adhesion, prosthesis liners are formed from at least one solid material layer not permeable to air, which seals off the limb stump and the inside of the prosthesis shaft from the surroundings in order to form a vacuum. The drawback to known prosthesis liners made from elastomer material is generally the intolerance of the sealing elastomer or rubber by the surface of the skin. When being worn, the inevitable activity of sebaceous and especially sweat glands in the living skin results in the detrimental formation of moisture between the skin of the limb stump and the inside of the prosthesis liner. This produces a subjective discomfort in the wearing and thus lessens the compliance in the wearing of the prosthesis which is necessary for medical purposes and for reasons of safety. On the other hand, the formation of moisture detrimentally results in a decrease in the adhesive friction between skin surface and liner, so that the risk exists of the prosthesis shaft being loosened or detached directly from the limb stump while being worn, which is associated with health risks for the prosthesis wearer, especially due to loss of control of the prosthesis, or, if applicable, of an artificial knee at the prosthesis. When walking, the risk of stumbling and falling is significantly increased. Moreover, with deficient adhesion between liner and skin surface, a usually topical but substantial frictional load occurs on the skin surface. If the skin has already been softened up by the moisture forming, skin irritation and injury may occur. Basically, the presence of moisture on the skin surface is a problem even at rest, because the skin surface is affected by this. This is highly critical especially in the case of scars or wounds. Besides general irritation and wound healing disturbance, infections of bacterial or fungal nature can also develop.

BRIEF SUMMARY OF THE INVENTION

Object of the invention was to improve known prosthesis liners in such a way that, on the one hand, the function of the prosthesis liner remains intact, but on the other hand the drawbacks of known prosthesis liners are lessened or entirely prevented, especially the formation of moisture between the skin of the limb stump and the prosthesis liner in place.

DESCRIPTION OF EXAMPLE EMBODIMENTS

For this, the invention proposes a novel prosthesis liner for application to a limb stump according to claim 1. According to the invention, this comprises at least one elastic liner layer made of elastomer, which according to the invention has pores at least in the region of the distal tip of the limb stump.

Preferably, it is provided that these pores are substantially closed in the relaxed state of the liner layer and become opened by stretching of the liner layer. This stretching is accomplished in particular when the prosthesis liner is applied on the stump, the prosthesis is put in place, and the prosthesis wearer uses the prosthesis in customary manner, i.e., transverse and shearing forces occur between the limb and the prosthesis shaft. For example, with a shin prosthesis or a thigh prosthesis there occurs a periodic stretching and relaxation of the liner layer while walking, so that the pores according to the invention are more or less widely opened or closed.

The prosthesis liner of the invention has pores which can produce an at least temporary gas-permeable and moisture-permeable connection between the inside of the liner facing the stump and the outside of the liner.

It turns out that, thanks to the pores according to the invention, the moisture and especially the sweat otherwise forming disadvantageously between the skin of the limb stump and the inside of the prosthesis liner can be drained through the liner layer to the outside, i.e., away from the skin surface. Advantageously, this drainage occurs especially during movement, i.e., upon stretching of the prosthesis liner. Without going in to the theory, the interplay of inherent elasticity of the liner layer and the change in the cross section of the pores dependent upon the stretching according to the invention produces a pump effect, which moves the formed moisture preferably actively to the outside. Advantageously, this prevents an excessive accumulation of naturally formed moisture, that is, especially sweat, on the skin surface of the limb stump. This is experienced by the prosthesis wearer directly as a significant increase in the wearing comfort. At the same time, the safety of use and the service life of the prosthesis is significantly increased.

Surprisingly, the pores according to the invention, contrary to expectation, do not result in a reduction of the otherwise desirable vacuum adherence of the prosthesis shaft to the limb stump. Instead, contrary to expectation, the adhesion-promoting effect of the prosthesis liner is improved by the pores, especially on account of the advantageous drainage of moisture.

In one preferred embodiment, the pores are arranged only in the distal portion of the prosthesis liner, i.e., in the area of the tip of the limb stump. In an alternative embodiment, the local density, that is the number of pores per area, is larger in the distal portion of the prosthesis liner than in the other portions of the prosthesis liner. In a preferred variant, alternatively or additionally, the presence of pores in a proximal portion of the prosthesis liner is precluded.

In another variant, the pores are distributed over the entire liner surface. In another variant, the pores are confined to certain zones, corresponding to anatomical structures of the underlying limb, i.e., they are present only there, or are present there in larger density. In particular, these zones are in areas of high sweat gland density. Conversely, in certain zones of the liner the occurrence of pores can be precluded, for example, for stability reasons. These are in particular zones of high mechanical tensile stress, such as in the region of the patella, the front edge of the shin bone, or the condyles.

Here, a "distal portion" refers to that region of the prosthesis liner which extends in the lengthwise direction, relative to the total extension of the prosthesis liner, for 70%, preferably 66%, especially preferably 40%, of the distal end of the prosthesis liner. A "proximal portion" here refers to that region of the prosthesis liner which extends in the lengthwise direction, relative to the total extension of the prosthesis liner, for the proximal 70%, preferably 50%, especially preferably 30%, of the proximal end of the prosthesis liner.

Preferably, the pores in the liner layer have a mean density of 2 to 20, especially 4 to 16 pores per $cm^2$ of area. Portions with "high density", on the other hand, have a density of around 8 to 20 pores per $cm^2$; zones with low density have a density of around 2 to 8 pores per $cm^2$.

The prosthesis liner according to the invention can be formed from all elastomer materials known for use in prosthesis liners. Preferably, the at least one elastic liner layer is formed from an elastomer which is chosen from among silicone elastomer (silicone rubber), polyurethane elastomer, chloroprene elastomer. Especially preferred is silicone elastomer, especially RTV silicone. The Shore hardness (A) is preferably from 20 to 50. The thickness of the liner layer is preferably 2 to 4 mm, in the case of so-called gel liners as much as 6 mm.

In an especially preferred embodiment, the pores in the liner layer are formed by chipless processes. These are preferably chosen from among machining steps such as slitting or piercing. In particular, this is done by the use of blades and/or needles. Especially in the formation of the pores by these chipless processes, it is guaranteed that the pores are substantially in the closed state in the relaxed, unstretched state of the prosthesis liner and can only be opened by a stretching stress. In the sense of the invention, this ensures an especially good valve action at the liner layer.

In an alternative embodiment, the pores are formed in the liner layer according to the invention by so-called chip-forming processes. These are preferably chosen from among the machining steps of punching and drilling. Chip-forming processes are understood to be material-removing processes. In this embodiment, therefore, the pores are formed with loss of material in the form of holes in the liner layer.

In an alternative embodiment, both holes formed by chip-forming processes and slits formed by chipless processes are present in the liner layer.

In a preferred variant, it is provided that the pores are provided exclusively or alternatively in high density in those regions of the liner layer of the prosthesis liner which can be positioned, in the worn state, over those regions of the limb stump where a high density of sweat glands is present and thus an increased formation of moisture is expected. In an alternative or additional embodiment, the pores are found exclusively or alternatively in high density in those regions of the liner layer where, in the worn state and during normal use, the moisture formed will follow the direction of gravity and build up on the inside of the prosthesis liner. This can be the distal tip of the limp stump, for example, in the case of a thigh or shin prosthesis.

In an alternative or additional embodiment, the pores according to the invention are formed as micropores in a liner layer which is itself an open-pore elastomer foam or contains such a foam. In one variant of this, the liner layer comprises both open-pore portions and closed-cell portions and/or cell-free portions. In terms of manufacturing technology, this can be accomplished for example by combined casting of foam and non-foam elastomer precursors in appropriate molds. A combination of porous foam elastomer and pores formed by chip-removing and/or chipless processes as described above is also conceivable here.

In one special embodiment it is provided that a layer of textile material is additionally arranged on the outside of the liner layer. This can be specially designed to enable or facilitate the gas exchange at the pores. Alternatively or additionally, the textile layer can be specially designed to take up moisture emerging from the pores and preferably transport it away or distribute it. In this way, one preferably ensures that the use between limb stump and prosthesis shaft can continue to be closed off entirely from the surroundings, which further improves the adhesion of the prosthesis shaft. It is especially provided that the textile material distributes, takes up and stores on the outside the moisture emerging locally on the outside of the prosthesis liner. Known processes and methods can now serve for the slow drainage or drying of the moisture formed, for example, during the resting phase of the prosthesis wearer, especially when no new sweat is being formed.

In one preferred variant of this, the textile layer is formed separately and is physically separate and can be removed from the liner layer of the prosthesis liner. In an alternative variant, the textile layer is firmly connected to the liner layer of the prosthesis liner as a unit. For this, the textile material can be glued to the liner layer or the liner layer of elastomer is polymerized onto the textile material.

The invention also concerns the use of the above characterized prosthesis liner for purposes of avoiding or lessening the formation of sweat on a limb stump of a patient when the prosthesis is put in place. It also concerns the use of a prosthesis liner as characterized in the foregoing claims for extending the effective time of wearing of the prosthesis on a patient.

The invention shall be described more closely by the following sample embodiments, without being considered to be limited to them.

FIG. 1 shows a schematic representation of the construction of a prosthesis liner 10 according to the invention. This is formed of at least one elastic liner layer 20 of elastomer material. According to the invention, the liner layer has pores 26 at least in a distal portion 30. The prosthesis liner 10 forms a sock-like sleeve, having an opening 44 at the proximal portion 40, which is pulled on over the limb stump.

Figure 2:
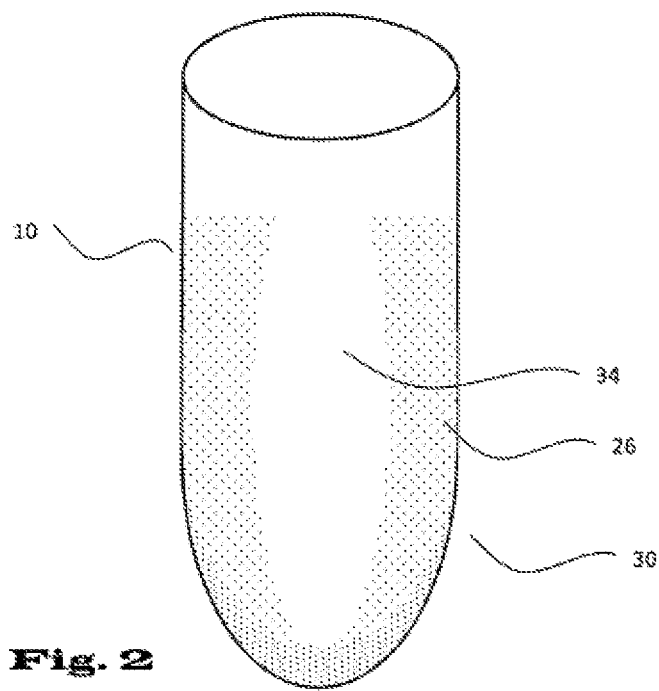

FIG. 2 shows in the representation of FIG. 1 a corresponding prosthesis liner 10, whose liner layer 20 has pores 26 at least in a distal portion 30, but not in certain zones 34 which can be exposed to particular mechanical loading.

Figure 3:
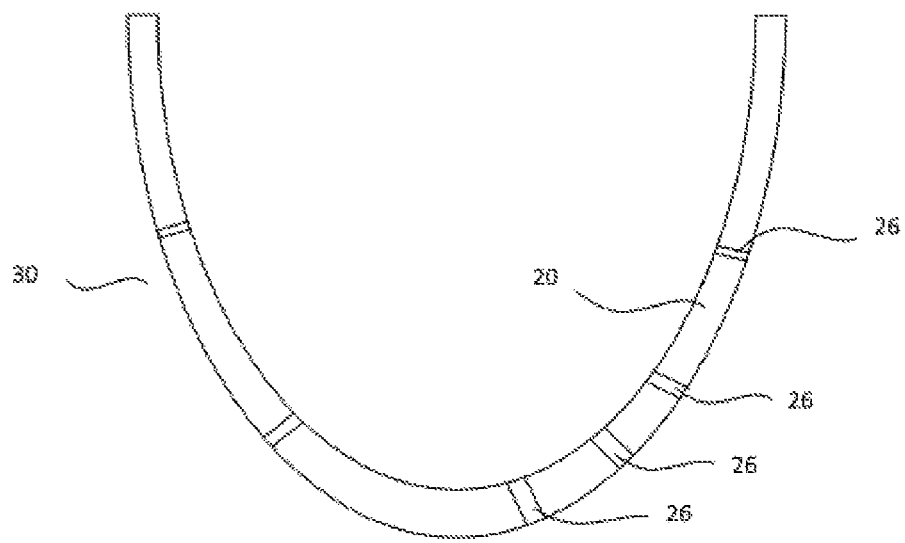
Figure 4:
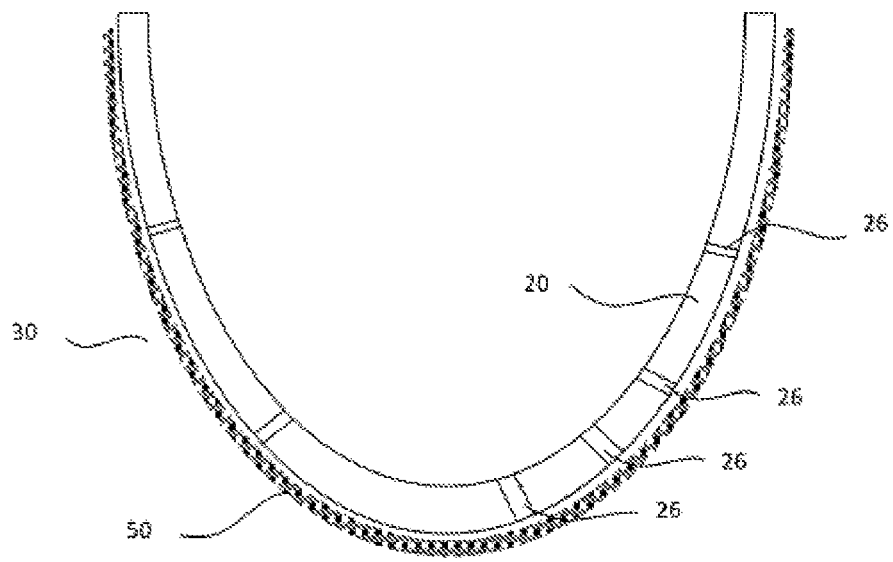

FIGS. 3 and 4 show a schematic detail view of the prosthesis liner 10 of FIG. 1 or 2. At least in the area of the distal portion 30 of the prosthesis liner there are pores 26 formed in the liner layer 20. FIG. 4 shows a preferred embodiment, wherein the liner layer 20 has an additional layer of textile material 50 lining it on the outside.

The invention claimed is:

1. Prosthesis liner for application to a limb stump, with an elastic liner layer of elastomer, wherein the liner layer has pores in at least one distal portion thereof, wherein the pores are closed in a relaxed state of the liner layer and become opened by stretching of the liner layer on the limb stump during movement.

2. Prosthesis liner according to claim 1, wherein the pores can produce an at least temporary gas-permeable and moisture-permeable connection between the inside of the liner facing the stump and the outside of the liner upon stretching of the liner layer.

3. Prosthesis liner according to claim 1, wherein a textile material is arranged on the outside of the liner layer, said textile material being specially designed to enable gas exchange at the pores and/or to take up moisture emerging from the pores.

4. Prosthesis liner according to claim 3, wherein the textile material is physically separate and can be removed from the liner layer.

5. Prosthesis liner according to claim 3, wherein the textile material is connected to the liner layer.

6. Prosthesis liner according to claim 1, wherein the pores are arranged in the liner layer in a mean density of 2 to 20 per cm$^2$.

7. Prosthesis liner according to claim 1, wherein the pores are not present in a proximal portion of the liner.

8. Prosthesis liner according to claim 1, wherein the elastomer is selected from a group consisting of silicone elastomer and polyurethane elastomer.

9. Prosthesis liner according to claim 1, wherein the pores are slits formed in the liner layer by a chipless process selected from a group consisting of slitting and piercing.

* * * * *